United States Patent
Holman

(10) Patent No.: US 6,342,240 B1
(45) Date of Patent: Jan. 29, 2002

(54) DISINFECTANT AND ODORIZING SYSTEM FOR AN EVAPORATION COOLER

(76) Inventor: John S. Holman, 410 N. 1400 West, Salt Lake City, UT (US) 84116

(*) Notice: Subject to any disclaimer, the term of this patent is extended or adjusted under 35 U.S.C. 154(b) by 0 days.

(21) Appl. No.: 09/544,436

(22) Filed: Apr. 7, 2000

(51) Int. Cl.[7] .............................................. A01N 25/34
(52) U.S. Cl. ...................... 424/408; 424/409; 424/465; 424/451; 424/76.1
(58) Field of Search ............................... 424/76.1, 466, 424/451, 408, 455, 12; 264/4.1; 512/4

(56) References Cited

U.S. PATENT DOCUMENTS

| | | | |
|---|---|---|---|
| D190,729 S | 6/1961 | Carter | |
| 4,196,851 A | 4/1980 | Davis | |
| 4,642,197 A | 2/1987 | Kruse et al. | |
| 4,722,801 A | * 2/1988 | Bunczk et al. | ............... 252/106 |
| 5,071,706 A | * 12/1991 | Soper | ...................... 428/402.2 |
| 5,246,919 A | 9/1993 | King | |
| 5,286,377 A | 2/1994 | Galvan | |
| 5,401,419 A | * 3/1995 | Kocib | ......................... 210/697 |
| 5,817,337 A | 10/1998 | Desenna | |

* cited by examiner

Primary Examiner—Thurman K. Page
Assistant Examiner—Robert M. Joynes

(57) ABSTRACT

A disinfectant and odorizing system for an evaporation cooler for disinfecting and odorizing water within a reservoir of an evaporation cooler. The disinfectant and odorizing system for an evaporation cooler includes a mixture. The mixture comprises a disinfectant and an aromatic oil. A water soluble tablet is hollow and is filled with the mixture.

1 Claim, 1 Drawing Sheet

DISINFECTANT AND ODORIZING SYSTEM FOR AN EVAPORATION COOLER

BACKGROUND OF THE INVENTION

1. Field of the Invention

The present invention relates to odorizing tablets and more particularly pertains to a new disinfectant and odorizing system for an evaporation cooler for disinfecting and odorizing water within a reservoir of an evaporation cooler.

2. Description of the Prior Art

The use of odorizing tablets is known in the prior art. More specifically odorizing tablets heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,817,337; 4,642,197; 4,196,851; U.S. Des. Pat. No. 190,729; U.S. Pat. Nos. 5,286,377; and 5,246,919.

While these devices fulfill their respective, particular objectives and requirements, the aforementioned patents do not disclose a new disinfectant and odorizing system for an evaporation cooler. The inventive device includes a mixture. The mixture comprises a disinfectant and an aromatic oil. A water soluble tablet is hollow and is filled with the mixture.

In these respects, the disinfectant and odorizing system for an evaporation cooler according to the present invention substantially departs from the conventional concepts and designs of the prior art, and in so doing provides an apparatus primarily developed for the purpose of disinfecting and odorizing water within a reservoir of an evaporation cooler.

SUMMARY OF THE INVENTION

In view of the foregoing disadvantages inherent in the known types of odorizing tablets now present in the prior art, the present invention provides a new disinfectant and odorizing system for an evaporation cooler construction wherein the same can be utilized for disinfecting and odorizing water within a reservoir of an evaporation cooler.

The general purpose of the present invention, which will be described subsequently in greater detail, is to provide a new disinfectant and odorizing system for an evaporation cooler apparatus and method which has many of the advantages of the odorizing tablets mentioned heretofore and many novel features that result in a new disinfectant and odorizing system for an evaporation cooler which is not anticipated, rendered obvious, suggested, or even implied by any of the prior art odorizing tablets, either alone or in any combination thereof.

To attain this, the present invention generally comprises a mixture. The mixture comprises a disinfectant and an aromatic oil. A water soluble tablet is hollow and is filled with the mixture.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new disinfectant and odorizing, system for an evaporation cooler apparatus and method which has many of the advantages of the odorizing tablets mentioned heretofore and many novel features that result in a new disinfectant and odorizing system for an evaporation cooler which is not anticipated, rendered obvious, suggested, or even implied by any of the prior art odorizing tablets, either alone or in any combination thereof.

It is another object of the present invention to provide a new disinfectant and odorizing system for an evaporation cooler which may be easily and efficiently manufactured and marketed.

It is a further object of the present invention to provide a new disinfectant and odorizing system for an evaporation cooler which is of a durable and reliable construction.

An even further object of the present invention is to provide a new disinfectant and odorizing system for an evaporation cooler which is susceptible of a low cost of manufacture with regard to both materials and labor, and which accordingly is then susceptible of low prices of sale to the consuming public, thereby making such disinfectant and odorizing system for an evaporation cooler economically available to the buying public.

Still yet another object of the present invention is to provide a new disinfectant and odorizing, system for an evaporation cooler which provides in the apparatuses and methods of the prior art some of the advantages thereof, while simultaneously overcoming some of the disadvantages normally associated therewith.

Still another object of the present invention is to provide a new disinfectant and odorizing system for an evaporation cooler for disinfecting and odorizing water within a reservoir of an evaporation cooler.

Yet another object of the present invention is to provide a new disinfectant and odorizing system for an evaporation cooler which includes a mixture. The mixture comprises a disinfectant and an aromatic oil. A water soluble tablet is hollow and is filled with the mixture.

Still yet another object of the present invention is to provide a new disinfectant and odorizing system for an evaporation cooler that adds a fresh scent to air circulating through the evaporation cooler.

Even still another object of the present invention is to provide a new disinfectant and odorizing system for an evaporation cooler that contains lubrication oil for lubricating the pumps of the evaporation cooler.

These together with other objects of the invention, along with the various features of novelty which characterize the invention, are pointed out with particularity in the claims annexed to and forming a part of this disclosure. For a better understanding of the invention. its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
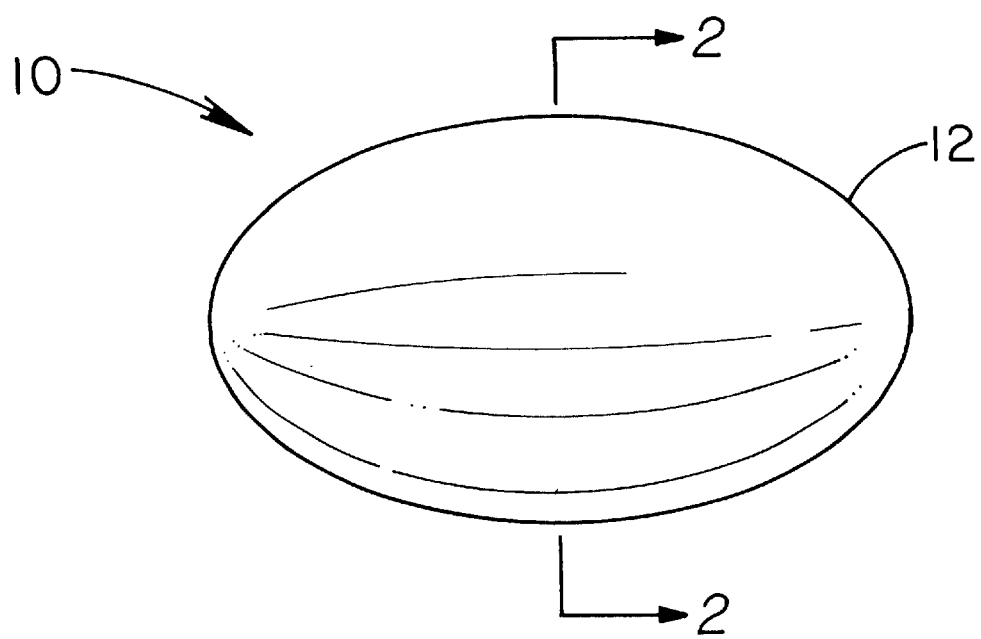
FIG. 1 is a schematic side view of a new disinfectant and odorizing system for an evaporation cooler according to the present invention.
Figure 2:
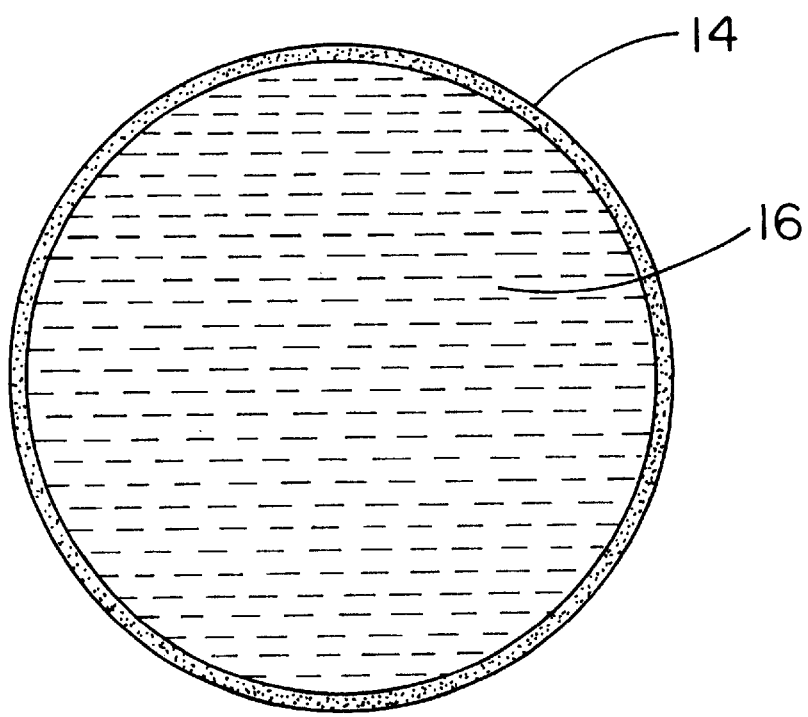
FIG. 2 is a schematic cross-sectional view taken along line 2—2 of the present invention.

With reference now to the drawings, and in particular to FIGS. 1 through 2 thereof, a new disinfectant and odorizing system for an evaporation cooler embodying the principles and concepts of the present invention and generally designated by the reference numeral 10 will be described.

As best illustrated in FIGS. 1 through 2, the disinfectant and odorizing system for an evaporation cooler 10 generally comprises a mixture 16 within a tablet 12. The tablet 12 is placed within an evaporation cooler, commonly known as a swamp cooler. The evaporation cooler contains a reservoir for holding water. The tablet 12 is water soluble and will disintegrate in the reservoir to spill the mixture 16 into the reservoir. Air is passed through the water as it cascades through the device. The air is cooled in the process and the cooled air is sent into the dwelling.

The mixture 16 contains a disinfectant, lubrication oil and aromatic oil. The disinfectant will ensure that bacteria does not grow in the reservoir. The lubrication oil will help to lubricate the pumps which move water about the evaporation cooler. The aromatic oil will odorize water which will transfer that odor to the air as it passes through the water. Thus sending pleasant smelling air throughout the dwelling. The ingredients of the mixture are all commercially available and no specific brand is required.

| The preferred mixture comprises by volume: | |
|---|---|
| disinfectant | 20%–50% |
| aromatic oil | 20%–50% |
| lubricating oil | 0%–80% |

| The ideal mixture comprises by volume: | |
|---|---|
| disinfectant | 33.33% |
| aromatic oil | 16.66% |
| lubricating oil | 50% |

Preferably, the disinfectant is alkyl dimethyl benzyl ammonium chloride, and the lubricating oil is a light lubricating oil.

Ideally the aromatic oil is oil derived from plants. Plant oils which work well include, but arc not limited to, rose, anise, caraway, chamomile, clove, coconut, eucalyptus, mint, lavender, lemon, orange, sassafras and sandalwood.

The tablet 12 comprises a shell 14. The tablet 12 is generally hollow. The internal area of the tablet may be from 2ml to 20ml, but preferably the internal area of the tablet 12 is substantially equal to 5 ml. The tablet 12 is generally water soluble such that it may dissolve in the reservoir.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described and accordingly, all suitable modifications and equivalents may be resorted to, falling within the scope of the invention.

I claim:

1. A disinfectant and odorizing system for disinfecting and odorizing water in an evaporation cooler, said system comprising:

a mixture, said mixture comprising;
33.33% by volume of a disinfectant, said disinfectant comprising alkyl dimethyl benzyl ammonium chloride;
16.66% by volume of an aromatic oil, said aromatic oil derived from plants, said plants being selected from the group consisting of rose, anise, caraway, chamomile, clove, coconut, eucalyptus, mint, lavender, lemon, orange, sassafras and sandalwood;
50% by volume of a lubricating oil;
a tablet, said tablet comprising a shell, said tablet being generally hollow, an internal area of said tablet being substantially equal to 5 ml, said tablet being generally water soluble; and
wherein said mixture being enclosed within said tablet such that said tablet with said mixture therein may be placed in the water in the evaporation cooler such that said tablet dissolves.

\* \* \* \* \*